US007758885B2

(12) United States Patent
Myhra

(10) Patent No.: US 7,758,885 B2
(45) Date of Patent: Jul. 20, 2010

(54) CLEANSING LOTION WITH MOISTURISING, PROTECTING AND ODOR CONTROLLING AGENTS AND CLOTH COMPRISING SAID LOTION

(75) Inventor: Medea Myhra, St. Peter, MN (US)

(73) Assignee: Coloplast A/S, Humlebaek (DK)

( * ) Notice: Subject to any disclaimer, the term of this patent is extended or adjusted under 35 U.S.C. 154(b) by 1155 days.

(21) Appl. No.: 11/272,018

(22) Filed: Nov. 14, 2005

(65) Prior Publication Data

US 2007/0110791 A1    May 17, 2007

(51) Int. Cl.
*A61K 9/70*    (2006.01)

(52) U.S. Cl. .................... 424/443; 424/70.22
(58) Field of Classification Search .............. None
See application file for complete search history.

(56) References Cited

U.S. PATENT DOCUMENTS

| 5,858,335 | A  | * | 1/1999  | Lucas et al. ............ 424/65 |
| 6,294,182 | B1 | * | 9/2001  | Znaiden et al. ......... 424/402 |
| 6,468,511 | B1 | * | 10/2002 | Chopra et al. .......... 424/65  |

* cited by examiner

*Primary Examiner*—Shanon A Foley
(74) *Attorney, Agent, or Firm*—Coloplast Corp., Coloplast A/S; Daniel G. Chapik; Nicholas R. Baumann

(57) ABSTRACT

The invention relates to a soothing lotion, which cleanses, moisturizes and protects the skin and controls odor from feces and urine on skin. The invention also relates to a cloth comprising said lotion.

15 Claims, No Drawings

CLEANSING LOTION WITH MOISTURISING, PROTECTING AND ODOR CONTROLLING AGENTS AND CLOTH COMPRISING SAID LOTION

FIELD OF THE INVENTION

The invention relates to a soothing lotion, which cleanses, moisturizes and protects the skin and controls odor from feces and urine on skin. The invention also relates to a cloth comprising said lotion.

BACKGROUND OF THE INVENTION

Baza Cleanse & Protect® with Odor Control is a well-known cleansing lotion comprising dimethicone as a skin protectant. For easy application to the skin, the product is typically provided in spray bottles. However, due to the reverse thixotrophic property of the lotion, plugging of the nozzle of the spray bottle can be a re-occurring problem.

It has now been found that it is possible to alter the recipe for the Baza Cleanse & Protect® with Odor Control to provide a new lotion with good odor control having a lower viscosity, which does not cause plugging of the nozzle in spray bottles.

It has also been found that the new lotion with lower viscosity may easily be incorporated in a cloth or wipe fabric. Lotions with higher viscosity may not be as easily incorporated into a cloth or wipe fabric.

Sage Products, Inc. and Medline Industries, Inc. market disposable washcloths comprising dimethicone. The disposable washcloth from Sage Products, Inc. is known as Sage® Comfort™ Shield™ Perineal-Care Washcloths, which comprises 3% dimethicone in a rayon/polyester blend needle-punch cloth. The product from Medline Industries, Inc. is known as Aloetouch One-Step Total Perineal Care, which comprises 3.2% dimethicone in a thin non-needlepunch cloth of a rayon/polyester blend.

It is well known in the industry, that rayon is blended with polyester to enhance absorption characteristics. A disadvantage of using a polyester/rayon blend can be that a cloth of a polyester/rayon blend comprising a cleansing lotion may tend to not release as much lotion to a surface during a cleansing event as a cloth comprised of 100% polyester.

It has been found that the new lotion of the invention is particularly suitable for incorporation into cloths or wipe fabric for preparing products useful for cleaning the surface, in particular the skin of a living being, and for controlling the odor from feces and urine on the skin, and for further providing a protective barrier to the skin.

In addition needle-punch cloth made of 100% polyester has been found to be particularly useful as it is capable of delivering twice as much lotion to the skin compared to the above mentioned polyester/rayon blended products, and is capable of maintaining comparable absorption characteristics.

SUMMARY OF THE INVENTION

Accordingly, the present invention relates to a cleansing lotion in the form of an emulsion comprising 75-85% w/w water, one or more skin protectants, such as dimethicone, one or more cleansing agents, and one or more odor control agents where the viscosity of the lotion is below 50,000 centipoise (cps) when measured on a Brookfield Digital viscometer models DV-1+ and DV-11+ at a temperature of 25° C.±1° C., using spindle T-C at a speed of 1.5 rpm.

The invention also relates to a cloth and a spray bottle comprising the new lotion. In particular the invention relates to a needle-punch, 100% polyester fiber cloth comprising the above mentioned lotion.

DETAILED DESCRIPTION OF THE INVENTION

Baza Cleanse & Protect® with Odor Control is a well-known cleansing lotion comprising dimethicone as a skin protectant agent.

It has been found, that by lowering the amount of cetearyl alcohol from 3% w/w and in particular by lowering the amount of zinc ricinoleate from 1% w/w in the known product, a lotion in the form of a stable emulsion with a viscosity suitable for incorporation of the lotion into a cloth may be obtained.

Surprisingly, it has been found that a good odor control may be achieved even when the amount of zinc ricinoleate is reduced considerably by the use of fragrances, such as Ordenone™. Ordenone™ is a fragrance available from Belle Aire Fragrances, Inc.

Accordingly, the present invention relates to a cleansing lotion in the form of an emulsion comprising 75-85% w/w water, one or more skin protectants, such as dimethicone, one or more cleansing agents, and one or more odor control agents where the viscosity of the lotion is below 50,000 centipoise (cps) as measured on a Brookfield Digital viscometer models DV-1+ and DV-11+ at a temperature of 25° C.±1° C., using spindle T-C at a speed of 1.5 rpm.

In a preferred embodiment of the invention, the cleansing lotion as above comprises zinc ricinoleate as an odor control agent and the amount of zinc ricinoleate in the lotion is below 1% w/w.

According to one embodiment of the invention, the new lotion comprises water, one or more emulsifiers or emulsion stabilizers, one or more skin protectants, such as dimethicone, one or more humectants, one or more emollients, one or more skin conditioners, one or more cleansing agents, one or more odor control agents, one or more preservatives, and optionally one or more pH controlling agents, in the form of an emulsion, where the composition comprises zinc ricinoleate as an odor control agent and the zinc ricinoleate is present in an amount below 1% w/w.

Suitably, the cleansing lotion of the invention comprises 75 to 85% w/w water, 3.0-5.5% w/w of one or more emulsifiers or emulsion stabilizers, 1-3% w/w of one or more skin protectants, such as dimethicone, 1-4% w/w of one or more humectants, 4-7% w/w of one or more emollients, 0.5-4% w/w of one or more skin conditioners, 1-3% w/w of one or more cleansing agents, 0.01-1.0% % w/w of one or more odor control agents, 0.42-0.8% w/w of one or more preservatives, and optionally one or more pH controlling agents. Preferably, the cleansing lotion as above comprises 1-3% w/w dimethicone.

The cleansing lotion of the invention may comprise cetearyl alcohol and glyceryl stearate as emulsifiers or emulsion stabilizers, isopropyl palmitate and glycine soja (soybean oil) as emollients, glycerin and panthenol as humectants, sodium lauroyl lactylate and propylene glycol as cleansing agent, allantoin and tocopheryl acetate as skin conditioners, methylparaben, propylparaben and diazolidinyl urea as preservatives, zinc ricinoleate, Ordenone™ and fragrance as odor control agents, and citric acid as pH controlling agent.

According to a preferred embodiment of the invention, the amount of cetearyl alcohol is below 3% w/w.

In the new recipe the amount of diazolidinyl urea may be also increased from 0.15% w/w to for example 0.30% w/w, compared to Baza Cleanse & Protect® with Odor Control.

Suitably, the cleansing lotion of the invention comprises 0.005-0.9% w/w zinc ricinoleate, suitably 0.005-0.1% w/w zinc ricinoleate, more preferred 0.005-0.05% w/w zinc ricinoleate, and most preferred 0.01% w/w zinc ricinoleate.

The lotion of the invention suitably comprises 0.1-0.5% w/w Ordenone™, preferably 0.1-0.3% w/w Ordenone™ or most preferred 0.2% w/w Ordenone™.

Thus, according to one preferred embodiment of the invention, the cleansing lotion comprises 0.005-0.05 w/w zinc ricinoleate, 0.1-0.5% w/w Ordenone™ and optionally an additional fragrance. If present, the additional fragrance is present in an amount of 0.1-0.3% W/w.

According to another preferred embodiment of the invention, the cleansing lotion comprises 0.005-0.05 w/w zinc ricinoleate, 0.1-0.3% w/w Ordenone™ and optionally an additional fragrance. If present, the additional fragrance is present in an amount of 0.1-0.3% w/w.

Even more preferred, the cleansing solution comprises 0.01 w/w zinc ricinoleate, 0.2% w/w Ordenone™ and optionally an additional fragrance. If present, the additional fragrance is present in an amount of 0.2% w/w.

The additional fragrance may suitably be Extra Fresh from Belle Aire Fragrances, Inc.

In a most preferred embodiment of the invention the composition of the new lotion is as stated in example 1 below.

With the cleansing lotion of the invention, plugging of the nozzles of the spray bottles containing the lotion may be avoided. An additional advantage of the lower viscosity of the new lotion is that it is particularly useful in allowing for easier impregnation of the lotion into the fiber-based cloths intended to be used as cleansing cloths.

Thus the invention also relates to a spray bottle and a cloth comprising the new cleansing lotion as described above.

The lotion of the invention may be incorporated into to the cloth by well known industrial processes for incorporation of emulsions into a cloth, e.g. by spraying, dipping, roller graver, etc.

The cloth is suitably made from one single type of synthetic polymer fiber, e.g. polypropylene or polyester fibers. Preferably, the cloth is made from 100% w/w polyester fiber, and suitably the polyester is a poly(oxy-1,2-ethanediyloxycarbonyl-1,4-phenylenecarbonyl).

The cloth may be a woven or non-woven cloth. Most preferred the cloth is a non-woven needle-punch cloth.

In a preferred embodiment the cloth is a 100% polyester (e.g. a poly(oxy-1,2-ethanediyloxycarbonyl-1,4-phenylenecarbonyl), staple fiber, crimped, needle-punch cloth, with the dimensions approximately 6-7 inches×10-11 inches with a weight of 2.25-3.85 oz/sy, preferably 2.5 oz/sy (85 g/m$^2$) and comprising 20-40 g, preferably 25-35 g, or most preferred 30 g of the new cleansing lotion of the invention.

Preferably the cloth is made from the 100% polyester fiber web, CS85PET-XX, CAS #25038-59-9 available from Sage Products, Inc.

The above mentioned, needle-punch cloth made of 100% polyester has been found to be particularly useful as it is capable of delivering twice as much lotion to the skin compared to the above mentioned polyester/rayon blended products.

The invention also relates to the use of the new cleansing lotion as described above for cleaning the surface, in particular the skin of a living being, and for controlling the odor from feces and urine on the skin, and for further providing a protective barrier to the skin.

The invention also relates to the use of the cloth as described above for cleaning the surface, in particular the skin of a living being, and for controlling the odor from feces and urine on the skin, and for further providing a protective barrier to the skin.

EXAMPLE 1

A modified cleansing lotion with lower viscosity may be prepared by mixing the following ingredients:

80.53-80.73% w/w water, USP grade
2.50% w/w cetearyl alcohol
2.50% w/w glyceryl stearate
2.00-2.20% w/w Dimethicone, NF grade, 1000 cs (centistokes) at 25° C.
2.00% w/w glycerin, USP grade
1.00% w/w panthenol
2.00% w/w sodium lauroyl lactylate and propylene glycol mixture (58% w/w sodium lauroyl lactylate and 42% w/w propylene glycol)
5.00% w/w isopropyl palmitate
0.20% w/w glycine soja (soybean) oil, USP grade
0.50% w/w allantoin
0.40% w/w tocopheryl acetate
0.01% w/w zinc ricinoleate
0.20% w/w Ordenone™, (Belle Aire Fragrances, Inc.)
0.20% w/w fragrance, Extra Fresh (Belle Aire Fragrances, Inc.)
0.30% w/w diazolidinyl urea
0.20% w/w methylparaben, NF/FCC grade
0.06% w/w propylparaben, NF/FCC grade
0.20% w/w citric acid, USP grade

EXAMPLE 2

A modified cleansing lotion with lower viscosity may be prepared by mixing the following ingredients:

82.13% w/w water, USP grade
1.00% w/w cetearyl alcohol
2.50% w/w glyceryl stearate
2.00% w/w Dimethicone, NF grade, 1000 cs (centistokes) at 25° C.
2.00% w/w glycerin, USP grade
1.00% w/w panthenol
2.00% w/w sodium lauroyl lactylate and propylene glycol mixture (58% w/w sodium lauroyl lactylate and 42% w/w propylene glycol)
5.00% w/w isopropyl palmitate
0.20% w/w glycine soja (soybean) oil, USP grade
0.50% w/w allantoin
0.40% w/w tocopheryl acetate
0.01% w/w zinc ricinoleate
0.20% w/w Ordenone™, (Belle Aire Fragrances, Inc.)
0.20% w/w fragrance, Extra Fresh (Belle Aire Fragrances, Inc.)
0.30% w/w diazolidinyl urea
0.20% w/w methylparaben, NF/FCC grade
0.06% w/w propylparaben, NF/FCC grade
0.30% w/w citric acid, USP grade

EXAMPLE 3

30 g of the lotion in example 1 is incorporated into a needlepunch cloth of 100% polyester fiber web, CS85PET- XX, CAS #25038-59-9 (Sage Products, Inc.), with the dimensions 6-7 inches×10-11 inches with a weight of 2.5 oz/sy (85 g/m$^2$).

EXAMPLE 4

25 g of the lotion in example 1 is incorporated into a needlepunch cloth of 100% polyester fiber web, CS85PET-XX, CAS #25038-59-9 (Sage Products, Inc.) with the dimensions 6-7 inches×10-11 inches with a weight of 2.5 oz/sy (85 g/m$^2$).

EXAMPLE 5

20 g of the lotion in example 1 is incorporated into a needlepunch cloth of 100% polyester fiber web, CS85PET-XX, CAS #25038-59-9 (Sage Products, Inc.) with the dimensions 6-7 inches×10-11 inches with a weight of 2.5 oz/sy (85 g/m$^2$).

EXAMPLE 6

35 g of the lotion in example 1 is incorporated into a needlepunch cloth of 100% polyester fiber web, CS85PET-XX, CAS #25038-59-9 (Sage Products, Inc.) with the dimensions 6-7 inches×10-11 inches with a weight of 2.5 oz/sy (85 g/m$^2$).

EXAMPLE 7

40 g of the lotion in example 1 is incorporated into a needlepunch cloth of 100% polyester fiber web, CS85PET-XX, CAS #25038-59-9 (Sage Products, Inc.) with the dimensions 6-7 inches×10-11 inches with a weight of 2.5 oz/sy (85 g/m$^2$).

EXAMPLE 8

40 g of the lotion in example 1 is incorporated into a needlepunch cloth of 100% polyester fiber web, (Sage Products, Inc.) with the dimensions 6-7 inches×10-11 inches with a weight of 3.5 oz/sy.

EXAMPLE 9

35 g of the lotion in example 1 is incorporated into a needlepunch cloth of 100% polyester fiber web, (Sage Products, Inc.) with the dimensions 6-7 inches×10-11 inches with a weight of 3.5 oz/sy.

EXAMPLE 10

30 g of the lotion in example 1 is incorporated into a needlepunch cloth of 100% polyester fiber web, (Sage Products, Inc.) with the dimensions 6-7 inches×10-11 inches with a weight of 3.5 oz/sy.

EXAMPLE 11

10 g of the lotion in example 1 is incorporated into a cloth of 100% polyester with the dimensions 6-7 inches×10-11 inches with a base weight of 2.0 oz.

EXAMPLE 12

15 g of the lotion in example 1 is incorporated into a cloth of 100% polyester with the dimensions 6-7 inches×10-11 inches with a base weight of 2.0 oz.

EXAMPLE 13

20 g of the lotion in example 1 is incorporated into a cloth of spunbound 100% polypropylene with the dimensions 6-7 inches×10-11 inches with a base weight of 1.0 oz.

EXAMPLE 14

15 g of the lotion in example 1 is incorporated into a cloth of spunbound 100% polypropylene with the dimensions 6-7 inches×10-11 inches with a base weight of 1.25 oz.

The invention claimed is:

1. A cleansing lotion comprising:
an emulsion comprising 75-85% w/w of water, at least one skin protectant, at least one cleansing agent, a fragrance and less than 0.05% w/w zinc ricinoleate, where the viscosity of the cleansing lotion is below 50,000 centipoise.

2. A cleansing lotion according to claim 1 and further comprising: an emulsion stabilizer, a humectant, an emollient, a skin conditioner, and a pH controlling agent.

3. The cleansing lotion according to claim 1 wherein the at least one skin protectant comprises between approximately 1-3% w/w dimethicone.

4. The cleansing lotion according to claim 1 comprising less than 0.05% and more than 0.005% zinc ricinoleate.

5. The cleansing lotion according to claim 4 comprising 0.1-0.5% w/w fragrance.

6. The cleansing lotion according to claim 5 comprising 0.1-0.3% w/w of a different second fragrance.

7. A spray bottle comprising a cleansing lotion according to claim 1.

8. A cloth comprising a cleansing lotion according to claim 1.

9. The cloth according to claim 8 wherein the cloth is made from one single type of synthetic polymer fibre.

10. The cloth according to claims 9 wherein the cloth is made from fibres of 100% polyester.

11. The cloth according to claim 10 wherein the polyester is poly(oxy-1,2-ethanediyloxycarbonyl1-1,4-phenylenecarbonyl).

12. The cloth according to claim 10 wherein the cloth is a needle-punch cloth.

13. The cloth according to claim 12 wherein the cloth comprises approximately 30 g of the cleansing lotion.

14. A package enclosing a number of cloths according to claim 8.

15. A cleansing lotion comprising:
an emulsion comprising 75-85% w/w of water, at least one skin protectant, at least one cleansing agent, and a fragrance and less than 0.05% w/w zinc ricinoleate, wherein the zinc ricinoleate enables the cleansing lotion to reduce skin odor.

* * * * *